US009034587B2

(12) United States Patent
Arber

(10) Patent No.: US 9,034,587 B2
(45) Date of Patent: May 19, 2015

(54) METHODS OF DIAGNOSING CANCER

(75) Inventor: Nadir Arber, Tel-Aviv (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 796 days.

(21) Appl. No.: 12/747,181

(22) PCT Filed: Dec. 10, 2008

(86) PCT No.: PCT/IL2008/001604
§ 371 (c)(1),
(2), (4) Date: Jun. 10, 2010

(87) PCT Pub. No.: WO2009/074988
PCT Pub. Date: Jun. 18, 2009

(65) Prior Publication Data
US 2010/0273191 A1    Oct. 28, 2010

Related U.S. Application Data

(60) Provisional application No. 60/996,881, filed on Dec. 10, 2007.

(51) Int. Cl.
*G01N 33/574* (2006.01)

(52) U.S. Cl.
CPC .... *G01N 33/57492* (2013.01); *G01N 33/57407* (2013.01); *G01N 33/57415* (2013.01); *G01N 33/57419* (2013.01); *G01N 33/57423* (2013.01); *G01N 33/5743* (2013.01); *G01N 33/57438* (2013.01); *G01N 33/57446* (2013.01)

(58) Field of Classification Search
None
See application file for complete search history.

(56) References Cited

U.S. PATENT DOCUMENTS

| 5,532,159 | A * | 7/1996 | Webb et al. | 435/344.1 |
| 5,962,237 | A * | 10/1999 | Ts'o et al. | 435/7.23 |
| 2004/0097448 | A1 | 5/2004 | Watt | |
| 2009/0253583 | A1* | 10/2009 | Yoganathan | 506/9 |
| 2011/0275079 | A1* | 11/2011 | Palma et al. | 435/6.12 |

FOREIGN PATENT DOCUMENTS

| WO | WO 03/079982 | 10/2003 |
| WO | WO 2007/088537 | 8/2007 |
| WO | WO 2009/074988 | 6/2009 |

OTHER PUBLICATIONS

Chan et al , Am J Obstet Gynecol, 2007, 507 e1-e5.*
Oie, J Cell Biochem,1996, Suppl 24:24-31.*
Orntoft et al, Mol Cell Proteomics, 2002, 1:37-45.*
Office Action Dated May 30, 2012 From the Israel Patent Office Re. Application No. 206051 and Its Translation Into English.
International Preliminary Report on Patentability Dated Jun. 24, 2010 From the International Bureau of WIPO Re. Application No. PCT/IL2008/001604.
Sagiv et al. "CD24 Is a Novel Oncogene in Colorectal Cancer, Detected by Microarray Profiling of Cell Transformation, and Is a Target for Immunotherapy of Cancer", Gastroenterology, XP009088622, 130(4/Suppl.2): A680/W1549, Apr. 1, 2006. Abstract.
International Search Report Dated Mar. 12, 2009 From the International Searching Authority Re.: Application No. PCT/IL2008/001604.
Written Opinion Dated Mar. 12, 2009 From the International Searching Authority Re.: Application No. PCT/IL2008/001604.
DePrimo et al. "Expression Profiling of Blood Samples From an SU5416 Phase III Metastatic Colorectal Cancer Clinical Trial: A Novel Strategy for Biomarker Identification", BMC Cancer, BioMed Central, XP021016079, 3(1): 1-12, Feb. 7, 2003. Abstract.
Sagiv et al. "CD24 Is a New Oncogene, Early at the Multistep Process of Colorectal Cancer Carcinogenesis", Gastroenterology, XP005587457, 131(2): 630-639, Aug. 1, 2006. p. 634-638.
Sagiv et al. "CD24 Plays an Important Role in the Carcinogenesis Process of the Pancreas", Biomedicine and Pharmacotherapy, XP025163398, 60(6): 280-284, Jul. 1, 2006. Abstract.
Smith et al. "The Metastasis-Associated Gene CD24 Is Regulated by Ral GTPase and Is a mediator of Cell Proliferation and Survival in Human Cancer", Cancer Research, XP002468864, 66(4): 1917-1922, Feb. 15, 2006. Abstract.
Communication Pursuant to Article 94(3) EPC Dated Oct. 1, 2013 From the European Patent Office Re. Application No. 08859782.8.
Office Action Dated Jul. 17, 2013 From the Israel Patent Office Re. Application No. 206051 and Its Translation Into English.

* cited by examiner

*Primary Examiner* — Mark Halvorson

(57) ABSTRACT

A method of diagnosing cancer or a pre-malignant lesion is disclosed. The method comprises determining a level of CD24 expressed on peripheral blood cells of a subject in need thereof, wherein the level of CD24 above a predetermined threshold is indicative of the cancer or the pre-malignant lesion.

9 Claims, 8 Drawing Sheets

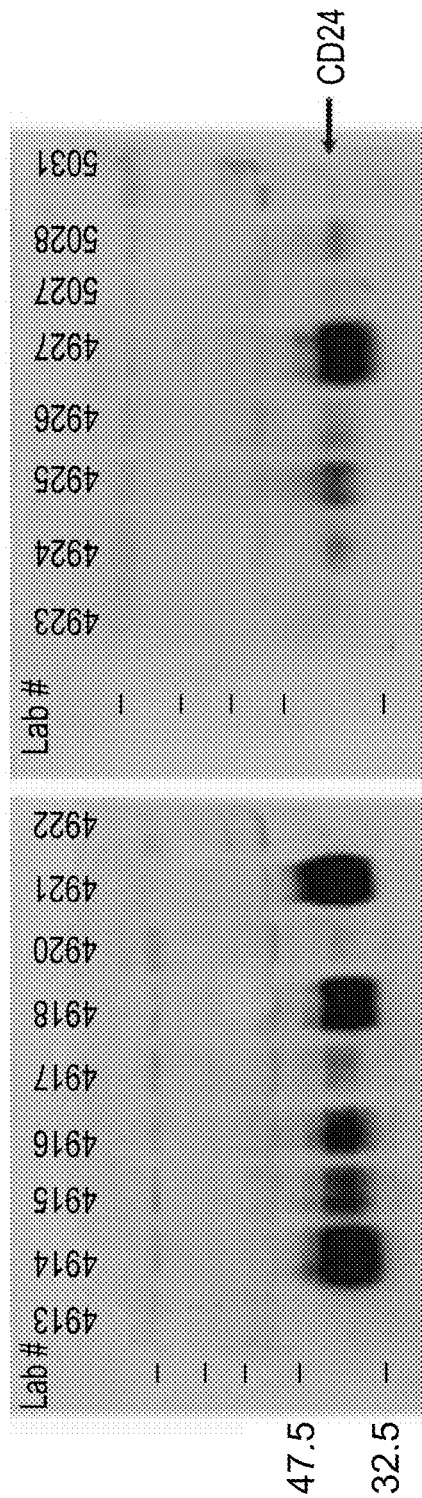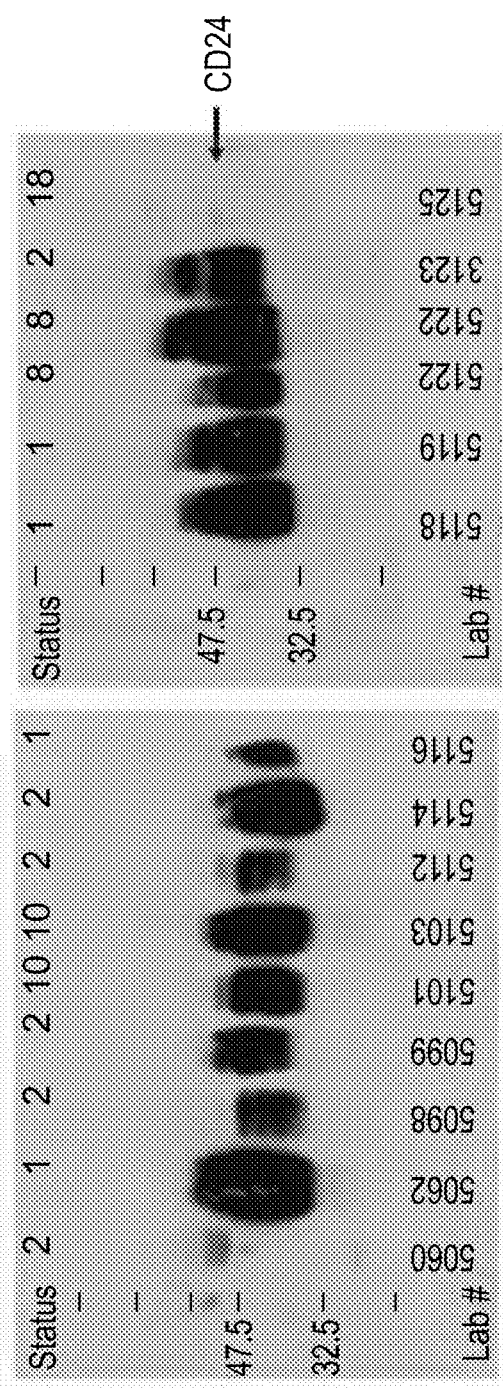
FIG. 1A FIG. 1B FIG. 1C FIG. 1D

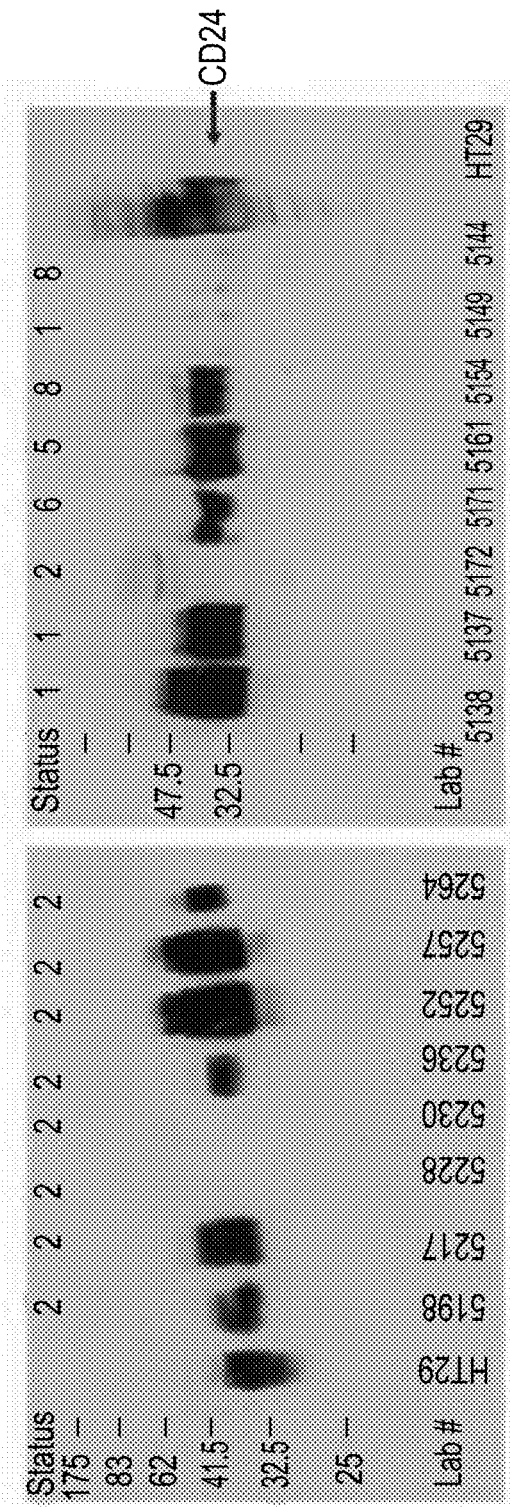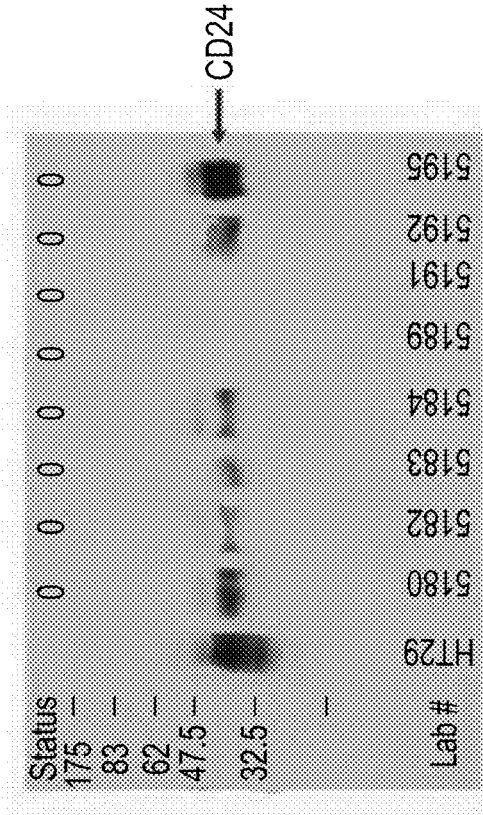

METHODS OF DIAGNOSING CANCER

RELATED APPLICATIONS

This Application is a National Phase of PCT Patent Application No. PCT/IL2008/001604 having International filing date of Dec. 10, 2008, which claims the benefit of U.S. Provisional Patent Application No. 60/996,881 filed on Dec. 10, 2007. The contents of the above Applications are all incorporated herein by reference.

FIELD AND BACKGROUND OF THE INVENTION

The present invention relates to methods for diagnosing cancer or pre-disposition to same by determining the expression level of CD24 in a sample of peripheral blood cells.

Colorectal cancer (CRC) is a major health concern in the Western world as it is the third most common cancer in both men and women in the United States and Israel. This form of cancer develops through a stepwise process that involves a variety of genetic and epigenetic changes that are acquired over several years and eventually culminate in the transformation of normal epithelium into neoplasm. Although the disease has a long latency period, the currently available markers for disease detection are limited to invasive tests such as colon or gastric endoscopy, which often detect the disease while it has already been spread.

Mutations in oncogenes and tumor suppressor genes, abnormal gene expression and genetic defects in a variety of genes are intimately involved in CRC carcinogenesis. On the basis of the allelotypes of a series of colon tumors, Vogelstein and colleagues [Vogelstein B, Fearon E R, Kern S E, et al.: Science 244 (4901): 207-11, 1989; Vogelstein B, Fearon E R, Hamilton S R, et al. Genetic alterations during colorectal-tumor development. *N Engl J Med* 319(9): 525-32, 1988] have shown that the molecular steps that occur after the activation of the APC-β-catenin-Tcf pathway involve a nonlinear accumulation of specific genetic changes that accompany the transition from normal colonic mucosa to metastatic carcinoma. These include mutations in the k-Ras oncogene, changes in methylation patterns, loss of DCC (Deleted in Colorectal Cancer gene) and SMADs [homologs of *drosophila* Mothers Against Decapentaplegic (MAD) protein, and the *C. elegans* protein SMA] and mutations in p53.

The currently available screening methods for cancers of the gastrointestinal tract (GI tract) such as colorectal cancer (CRC) include fecal occult blood testing (FOBT). However, although clinical trials have shown that screening with serial FOBT reduces CRC mortality (Mandel J, et al., 1993), the sensitivity of FOBT is limited [60%; McMahon P M, et al., 2001]. Several markers have been recently suggested as non-invasive diagnostic tools. These include proteins [e.g., fecal calprotectin, lactoferrin, lysozyme, albumin, alpha-1-antitrypsin, carcinoembryonic antigen (CEA), decay-accelerating factor (DAF), minichrosomal maintenance protein (MCM2)] or mRNA (e.g., fecal COX-2) (Kanaoka S., et al., 2004) which can be detected in stool samples, and proteins such as nicotinamide N-methyltransferase (NNMT) (Roessler M, et al., 2005) or proteasome activator complex subunit 3 (PSME3) (Roessler M., et al., 2006), which can be detected in serum samples. However, due to their low sensitivity and specificity, these markers are not in clinical use.

CD24, also known as heat-stable antigen (HSA) in mice, is a heavily glycosylated phosphatidylinositol-anchored mucin-like cell-surface protein. Physiologically, the CD24 protein is expressed mainly on hematopoietic subpopulations of B-lymphocytes, various epithelial cells, muscle and neural cells. It plays a crucial role in cell selection and maturation during hematopoiesis and is expressed during the embryonic period, on developing neural and pancreatic cells. In addition, CD24 is a potential ligand for P-selectin which functions as an adhesion molecule that enhances platelets aggregation.

The cellular function of CD24 is still unknown, but recent reports have strengthened its involvement in the initiation of intracellular signal transduction. Schabath et al. (Schabath H, et al., 2006) have associated the expression of CD24 with downregulation in the CXCR-4 chemokine receptor. In addition, CD24 is overexpressed in various malignant tissues including B-cell lymphomas, gliomas, small-cell and non-small cell lung, hepatocellular, renal cell, nasopharyngeal, bladder, uterine, epithelial ovarian, breast, prostate and pancreatic carcinomas (reviewed by Kristiansen et al., 2004). Moreover, its expression was found to correlate with increased growth rate, motility and survival in carcinoma cell lines derived from several organs (Baumann P, et al., 2005; Smith S C, et al., 2006) and with a more aggressive course of cancer. Thus, Weichert W., et al. (2005), found that increased expression of CD24 in the cytoplasm correlates with higher tumor stage, grade and presence of metastasis and concluded that overexpression of CD24 in the cytoplasm (as a result of over production or disturbances in distribution in the cell) is a marker for poorer prognosis. In addition, the role of CD24 in platelet aggregation may explain the involvement with cancer metastases and worse prognosis (Sammar, M., et al., 1994; Aigner, S., et al., 1997; Aigner, S., et al., 1998).

U.S. Pat. Appl. 20040005596 to Li J., et al., discloses methods of diagnosing cancer by determining the level of CD24 in situ in tissue samples suspected to be precancerous or cancerous, thus again necessitating invasional procedures for cancer detection.

International Patent Publication No. WO2007/088537 teaches methods of diagnosing cancer by determining the level of circulating, non-anchored CD24 in a subject.

SUMMARY OF THE INVENTION

According to an aspect of some embodiments of the present invention there is provided a method of diagnosing cancer or a pre-malignant lesion, the method comprising determining a level of CD24 expressed on peripheral blood cells of a subject in need thereof, wherein the level of CD24 above a predetermined threshold is indicative of the cancer or the pre-malignant lesion.

According to an aspect of some embodiments of the present invention there is provided a method of determining a predisposition to cancer or a pre-malignant lesion, the method comprising determining a level of CD24 expressed on peripheral blood cells of a subject in need thereof, wherein the level of CD24 above a predetermined threshold is indicative of a predisposition to the cancer or the pre-malignant lesion.

According to some embodiments of the invention, the pre-malignant lesion is an adenoma.

According to some embodiments of the invention the determining is effected ex vivo.

According to some embodiments of the invention, the pre-malignant lesion is associated with a solid tumor.

According to some embodiments of the invention, the cancer is a solid tumor.

According to some embodiments of the invention, the pre-malignant lesion is associated with a gastrointestinal tract cancer.

According to some embodiments of the invention, the cancer is a gastrointestinal tract cancer.

According to some embodiments of the invention, the gastrointestinal tract cancer is colorectal cancer.

According to some embodiments of the invention, the gastrointestinal tract cancer is colorectal cancer.

According to some embodiments of the invention, the cancer is breast cancer.

According to some embodiments of the invention, the cancer is lung cancer.

According to some embodiments of the invention, the cancer is prostate cancer.

According to some embodiments of the invention, the cancer is a pancreatic cancer.

According to some embodiments of the invention, the cancer is a skin cancer.

According to some embodiments of the invention, the cancer is a urinary tract cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-G are scans of Western blot analyses of PBL cell lysates using anti-CD24 SWA11 antibody for immunodetection. Status numbers of individuals tested indicate the disease states as follows: 0—Normal healthy subjects; 1—patients with adenomas; 2—CRC; 3—Pancreatic carcinoma; 5—Barret's disease; 6—Gastric carcinoma; 8—Other tumors; 10—Breast cancer; IBD (4)—Inflammatory bowel disease. HT29 cell lysate served as positive control.

FIG. 2A: Normal vs. Adenomas, CRC, and IBD. FIG. 2B: Normal vs. various cancers. Bar-graphs represent band volumes as determined by optical density (OD) units. Total number of bands scanned was 56.

DESCRIPTION OF SPECIFIC EMBODIMENTS OF THE INVENTION

The present invention, in some embodiments thereof, relates to methods for diagnosing cancer or pre-disposition to same by determining the expression level of CD24 in a sample of peripheral blood cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cancers of the gastrointestinal (GI) tract, including colorectal cancer (CRC), develop over several years through a stepwise process in which genetic and epigenetic changes are acquired and eventually culminate in the transformation of normal epithelium into neoplasm. For example, CRC carcinogenesis involves mutations in oncogenes (e.g., k-Ras) and tumor suppressor genes (e.g., p53), changes in methylation patterns and loss of DCC and SMADs. However, in spite of the current genetic knowledge and the currently available endoscopy procedures (e.g., colonoscopy), at the time of diagnosis most of GI tract-related cancers have already spread and are more difficult to treat.

While reducing the present invention to practice, the present inventors have uncovered that CD24 is over-expressed on the peripheral blood cells (PBCs) of a subject suffering from, or even predisposed to cancer.

Figure 2A:
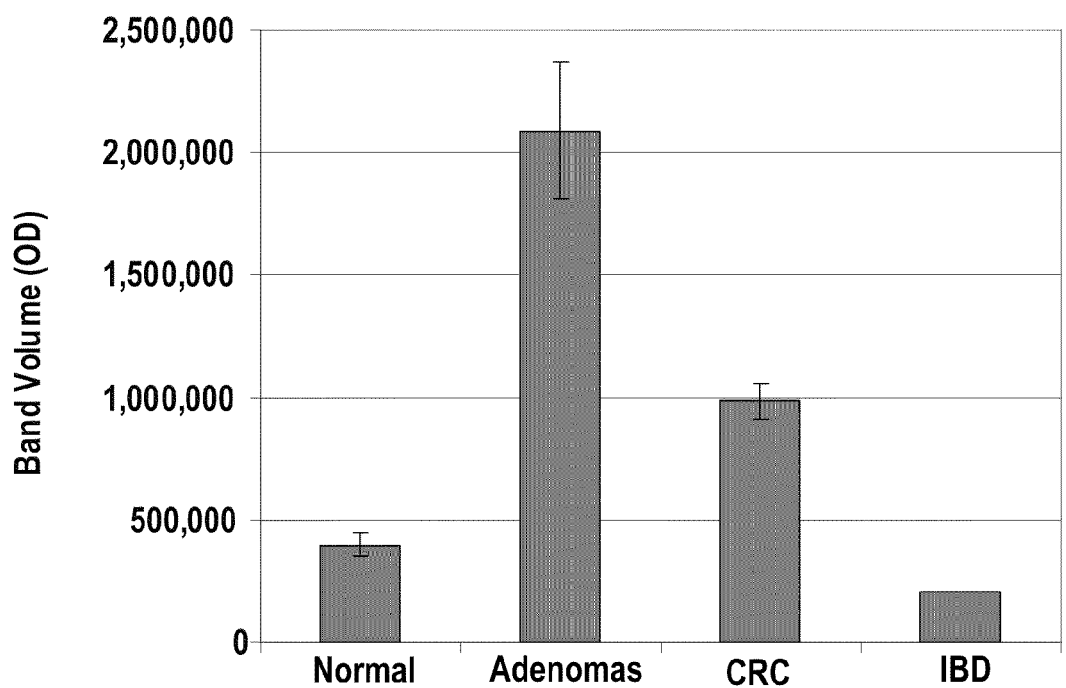
FIGS. 2A-B are bar graphs illustrating the results of a densitometry analysis of the blots shown in FIGS. 1A-G. The blots were analyzed by densitometry using ImageMaster 1D Gel Analysis v4.10.
Figure 2B:
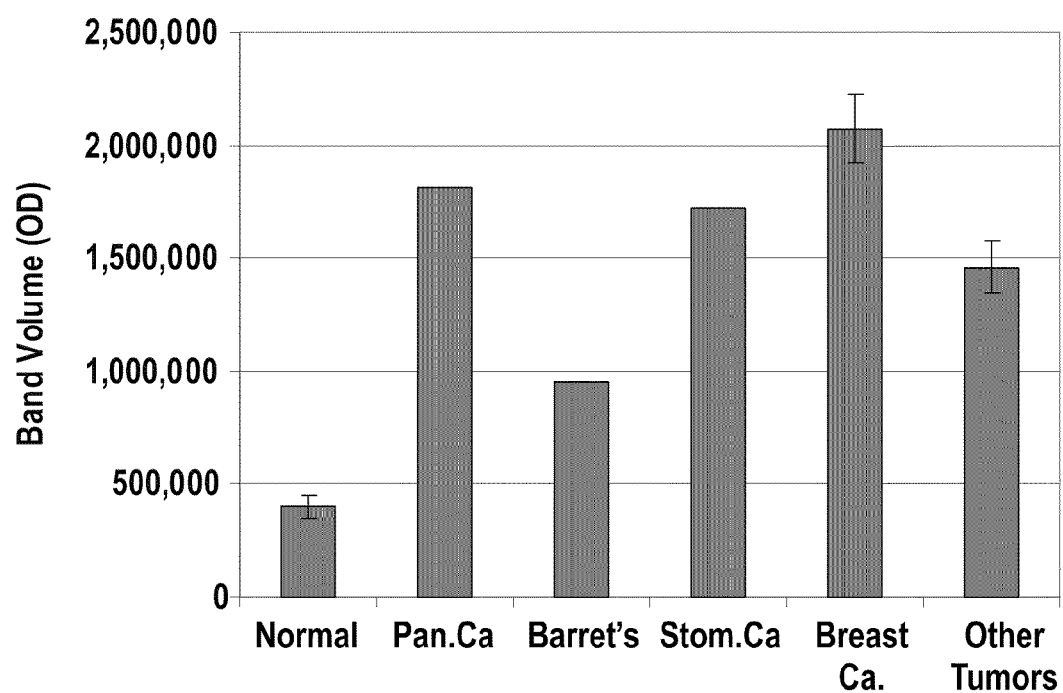
Figure 5:
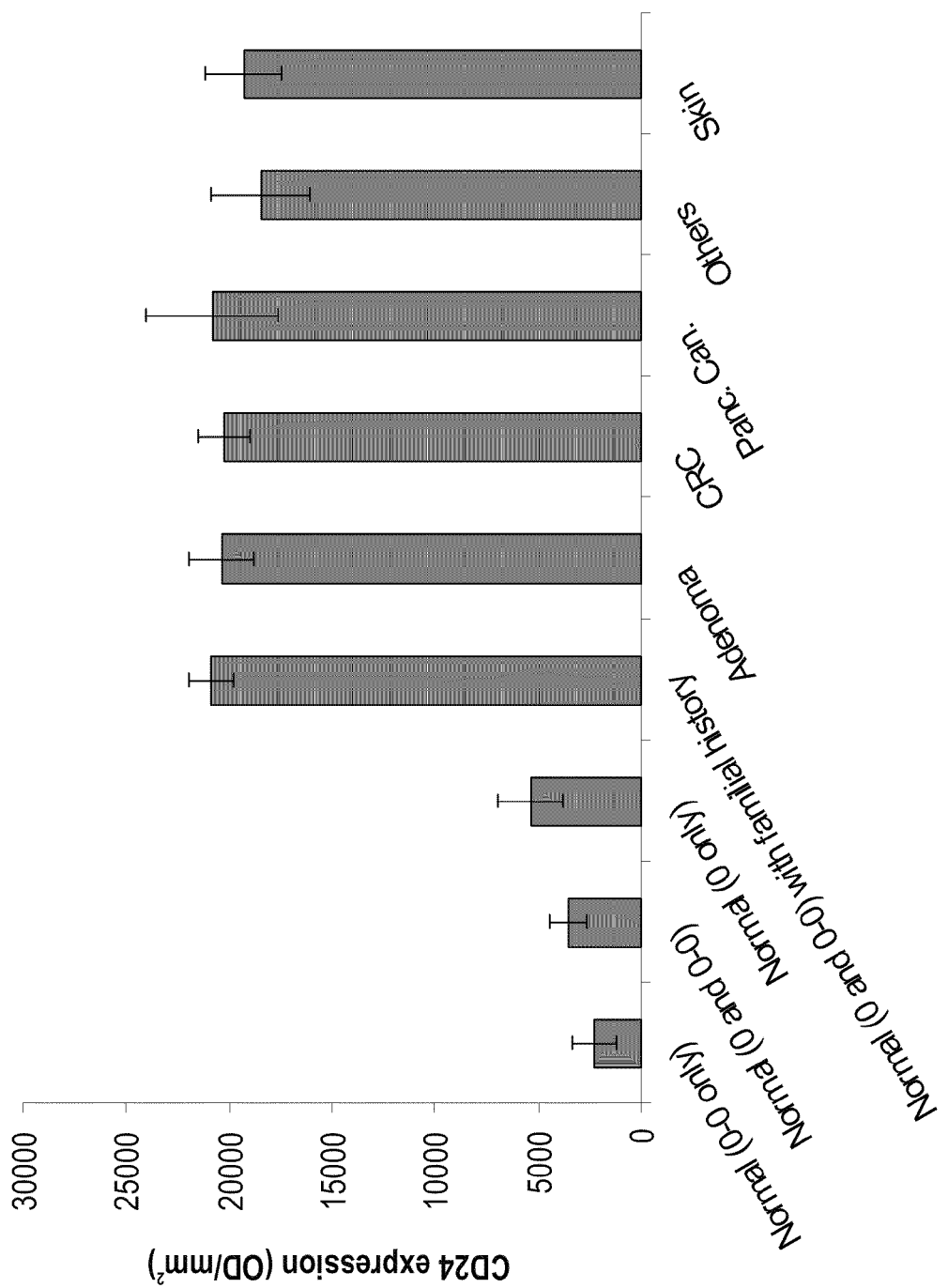
FIG. 5 is a bar graph illustrating the results of a densitometry analysis of Western blot analyses of PBL cell lysates using anti-CD24 SWA11 antibody for immunodetection.

As is shown in the Examples section which follows, patients suffering from colorectal cancer, adenomas, stomach cancer, pancreatic cancer, skin cancer, breast cancer, Barret's and other forms of cancer all have an elevated level of CD24 on their PBCs (FIGS. 2A-B and FIG. 5).

The present inventors have shown that the CD24 levels for adenoma are such that the sensitivity and accuracy of a diagnostic method which is based on measuring the expression level of CD24 on PBCs is at least 75% and 73% respectively. The levels for colorectal cancer (CRC) are such that the sensitivity and specificity of a diagnostic method which is based on measuring the expression level of CD24 on PBCs is at least 70% and 83% respectively.

Thus, according to one aspect of the present invention, there is provided a method of diagnosing cancer or a pre-malignant lesion, the method comprising determining a level of CD24 expressed on peripheral blood cells of a subject in need thereof, wherein the level of CD24 above a predetermined threshold is indicative of the cancer or the pre-malignant lesion.

As used herein, the term "diagnosing" refers to classifying a pathology (e.g., a 0024-associated cancer or a pre-malignant lesion) or a symptom, determining a severity of the pathology, monitoring pathology progression, forecasting an outcome of a pathology and/or prospects of recovery.

As used herein, the phrase "pre-malignant lesion" refers to a mass of cells and/or tissue having increased probability of transforming into a malignant tumor. Preferably, in the pre-malignant lesion of the present invention CD24 is over-expressed as compared to a non-malignant tissue or cell. Examples of pre-malignant lesions include, but are not limited to, adenomatous polyps, Barrett's esophagus, IPMN (Intraductal Papillary Mucinus Neoplasia), DCIS (Ductal Carcinoma in Situ) in the breast, leukoplakia and erythroplakia. Thus, the pre-malignant lesion which is diagnosed according to the method of this aspect of the present invention can transform into a malignant solid or non-solid (e.g., hematological malignancies) CD24-associated cancer (or tumor). Preferably, the pre-malignant lesion which is diagnosed by the method of this aspect of the present invention is an adenomatous polyp of the colon, an adenomatous polyp of the rectum, an adenomatous polyp of the small bowel and Barrett's esophagus.

Non-limiting examples of CD24-associated cancers which can be diagnosed by the method of this aspect of the present invention include tumors of the gastrointestinal tract (colon cancer, rectum cancer, anal region cancer, colorectal cancer, small and/or large bowel cancer, esophageal cancer, stomach cancer, pancreatic cancer, gastric cancer, small intestine cancer, adenocarcinoma arising in the small intestine, carcinoid tumors arising in the small intestine, lymphoma arising in the small intestine, mesenchymal tumors arising in the small intestine, gastrointestinal stromal tumors), gallbladder carcinoma, Biliary tract tumors, prostate cancer, kidney (renal) cancer (e.g., Wilms' tumor), liver cancer (e.g., hepatoblastoma, hepatocellular carcinoma), hepatobiliary cancer, biliary tree cancer, tumors of the Gallbladder, bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian cancer, cervical cancer, cancer of the vagina, cancer of the Vulva, lung cancer (e.g., small-cell and non-small cell lung carcinoma), nasopharyngeal, breast cancer, squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic, cutaneous T-cell lymphoma, primary central nervous system lymphoma), gliomas, medullary thyroid carcinoma, testicular cancer, brain and head/neck cancer, gynecologic cancer, endometrial cancer, germ cell tumors, mesenchymal tumors, neurogenic tumors, cancer of the bladder, cancer of the ureter, cancer of the renal pelvis, cancer of the urethra, cancer of the penis, cancer of the testis, cancers of the uterine body, endometrial carcinoma, uterine sarcoma, peritoneal carcinoma and Fallopian Tube carcinoma, germ cell tumors of the ovary, sex cord-stromal tumors, cancer of the endocrine system, thyroid tumors, medullary thyroid carcinoma, thyroid lymphoma, parathyroid tumors, adrenal tumors, pancreatic endocrine tumors, sarcomas of the soft tissue and bone, benign and malignant mesothelioma, malignant peritoneal mesothelioma, malignant mesothelioma of the Tunica Vaginalis Testis, malignant mesothelioma of the Pericardium, skin cancer, cutaneous melanoma, intraocular melanoma, neoplasms of the central nervous system, medulloblastomas, meningiomas, peripheral nerve tumors, Pineal region tumors, pituitary adenomas, craniopharyngiomas, acoustic neuromas, Glomus Jugulare tumors, Chordomas and Chondrosarcomas, Hemangioblastomas, Choroid Plexus Papillomas and Carcinomas, spinal axis tumors, leukemia, and chronic leukemia.

As used herein the phrase "subject in need thereof" refers to a human subject who is at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up.

As used herein the term "CD24" refers to the nucleic acid sequence and/or the amino acid sequence of at least a functional portion of the phosphatidylinositol-anchored mucin-like cell-surface protein (e.g., CD24 protein—SEQ ID NO:1, GenBank Accession No. NP_037362.1; CD24 transcript—SEQ ID NO:2, GenBank Accession No. NM_013230.2) encoded by a genomic sequence on chromosome 6q21.

According to this aspect of the present invention, the CD24 is present in a peripheral blood cell sample.

According to one embodiment, the CD24 is anchored to peripheral blood cells (i.e. it does not refer to free, non-anchored CD24).

As used herein, the phrase "peripheral blood cell sample" refers to a sample taken from circulating blood as opposed to blood cells sequestered within the lymphatic system, spleen, liver, or bone marrow.

Peripheral blood cell samples are typically taken a syringe with a needle.

Methods of processing peripheral blood cell samples are known in the art and further described in the Examples section herein below.

It will be appreciated that determining the level of CD24 in peripheral blood can be effected ex vivo (on a sample derived from the subject) as well as in vivo (within the subject).

As used herein, the phrase "level of CD24" refers to the degree of gene expression and/or gene product activity of the CD24 gene in the biological sample. Accordingly, the level of CD24 can be determined at the amino acid level using protein detection methods.

Thus, the level of the CD24 amino acid sequence (CD24 protein) can be determined using a CD24 specific antibody via the formation of an immunocomplex [i.e., a complex formed between the CD24 antigen (a CD24 amino acid sequence) present in the biological sample and the CD24 specific antibody].

The immunocomplex of the present invention can be formed at a variety of temperatures, salt concentration and pH values which may vary depending on the method and the biological sample used and those of skills in the art are capable of adjusting the conditions suitable for the formation of each immunocomplex.

The term "antibody" as used in this invention includes intact molecules as well as functional fragments thereof, such as Fab, F(ab')$_2$, Fv or single domain molecules such as VH and VL to an epitope of an antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to the method of this aspect of the present invention, an amount of immunocomplex formation is indicative of a diagnosis of the cancer or the pre-malignant lesion. Various methods can be used to detect the formation of the CD24 immunocomplex of the present invention and those of skills in the art are capable of determining which method is suitable for each immunocomplex.

The CD24 antibody used in the immunocomplex of the present invention can be labeled using methods known in the art. It will be appreciated that the labeled antibodies can be either primary antibodies (i.e., which bind to the specific antigen, e.g., a CD24-specific antigen) or secondary antibodies (e.g., labeled goat anti rabbit antibodies, labeled mouse anti human antibody) which bind to the primary antibodies. The antibody can be directly conjugated to a label or can be conjugated to an enzyme.

Antibodies of the present invention can be fluorescently labeled (using a fluorescent dye conjugated to an antibody), radiolabeled (using radiolabeled e.g., $^{125}$I, antibodies), or conjugated to an enzyme (e.g., horseradish peroxidase or alkaline phosphatase) and used along with a chromogenic substrate to produce a colorimetric reaction. The chromogenic substrates utilized by the enzyme-conjugated antibodies of the present invention include, but are not limited to, AEC, Fast red, ELF-97 substrate [2-(5'-chloro-2-phosphorylox-yphenyl)-6-chloro-4(3H)-quinazolinone], p-nitrophenyl phosphate (PNPP), phenolphthalein diphosphate, and ELF 39-phosphate, BCIP/INT, Vector Red (VR), salmon and magenta phosphate (Avivi C., et al., 1994, J. Histochem. Cytochem. 1994; 42: 551-4) for alkaline phosphatase enzyme and Nova Red, diaminobenzidine (DAB), Vector (R) SG substrate, luminol-based chemiluminescent substrate for the peroxidase enzyme. These enzymatic substrates are commercially available from Sigma (St Louis, Mo., USA), Molecular Probes Inc. (Eugene, Oreg., USA), Vector Laboratories Inc. (Burlingame, Calif., USA), Zymed Laboratories Inc. (San Francisco, Calif., USA), Dako Cytomation (Denmark).

Detection of the CD24 immunocomplex in PBCs can be performed using fluorescence activated cell sorting (FACS), enzyme linked immunosorbent assay (ELISA), Western blot and radio-immunoassay (RIA) analyses, immunoprecipitation (IP) or by a molecular weight-based approach.

For Western blot the proteins are extracted from a cell sample and are subjected to electrophoresis (e.g., SDS-PAGE) and blotting to a membrane (e.g., nitrocellulose or PVDF). The membrane is then interacted with a CD24 antibody which can be either directly labeled or further subjected to a secondary labeled antibody. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

In case the concentration of the antigen in the biological sample is low, detection of the antigen (CD24 amino acid sequence) can be performed by immunoprecipitation (IP). For immunoprecipitation analysis the CD24 antibody may directly interact with a sample (e.g., cell lysate) including CD24 and the formed complex can be further detected using a secondary antibody conjugated to beads (e.g., if the CD24 antibody is a mouse monoclonal antibody, the secondary antibody may be an anti-mouse antibody conjugated to e.g., Sepharose beads). The beads can be then precipitated by centrifugation, following which the precipitated proteins (e.g., CD24 and anti CD24 antibodies) can be detached from the beads (e.g., using denaturation at 95° C.) and further subjected to Western blot analysis using the CD24 specific antibodies. Alternatively, the anti-CD24 antibody and the beads-conjugated secondary antibody may be added to the biological sample containing the antigen (CD24) to thereby form an immunocomplex. Alternatively, since CD24 is a highly glycosylated protein, it can be also precipitated using a substrate capable of binding glycosylated polypeptides such as Concavalin A (GE Healthcare Bio-Sciences, Uppsala, Sweden) which may be also conjugated to beads, followed by Western blot analysis with anti-CD24 antibodies.

FACS analysis enables the detection of antigens present on cell membranes such as CD24. Briefly, CD24 specific antibodies are linked to fluorophores and detection is performed by means of a cell sorting machine which reads the wavelength of light emitted from each cell as it passes through a light beam. This method may employ two or more antibodies simultaneously.

The level of CD24 can be also determined using ELISA. Briefly, a sample containing CD24 antigen is fixed to a surface such as a well of a microtiter plate. An antigen specific antibody (a CD24 antibody) coupled to an enzyme is applied and allowed to bind to the antigen. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

The level of CD24 can be also determined using radio-immunoassay (RIA). In one version, this method involves precipitation of the desired antigen (CD24) with a specific antibody and radiolabeled antibody binding protein (e.g., protein A labeled with $I^{125}$) immobilized on a precipitable carrier such as agarose beads. The number of counts in the precipitated pellet is proportional to the amount of antigen.

In an alternate version of the RIA, a labeled antigen and an unlabelled antibody binding protein are employed. A sample containing an unknown amount of antigen is added in varying amounts. The decrease in precipitated counts from the labeled antigen is proportional to the amount of antigen in the added sample.

The level of CD24 can be also determined using molecular weight-based approach. Since the immunocomplex exhibits a higher molecular weight than its components, methods capable of detecting such a change in the molecular weight can be also employed. For example, the immunocomplex can be detected by a gel retardation assay. Briefly, a non-denaturing acrylamide gel is loaded with samples. A shift in the size (molecular weight) of the protein product as compared with its components is indicative of the presence of an immunocomplex. Such a shift to a higher molecular weight can be viewed using a non-specific protein staining such as silver stain or Commassie blue stain.

It will be appreciated that analyzing an amount of CD24 in PBCs may also be effected on the polynucleotide level. RNA detection methods can be performed using an isolated polynucleotide (e.g., a polynucleotide probe, an oligonucleotide probe/primer) capable of hybridizing to a CD24 nucleic acid sequence such as the CD24 transcript set forth by SEQ ID NO:2 or a portion thereof. Such a polynucleotide can be at any size, such as a short polynucleotide (e.g., of 15-200 bases), an intermediate polynucleotide of 100-2000 bases and a long polynucleotide of more than 2000 bases.

The isolated polynucleotide probe used by the present invention can be any directly or indirectly labeled RNA molecule [e.g., RNA oligonucleotide (e.g., of 17-50 bases), an in vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to the CD24 RNA transcript of the present invention.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The isolated polynucleotide used by the present invention can be labeled either directly or indirectly using a tag or label molecule. Such labels can be, for example, fluorescent molecules (e.g., fluorescein or Texas Red), radioactive molecule (e.g., $^{32}P$-γ-ATP or $^{32}P$-α-ATP) and chromogenic substrates [e.g., Fast Red, BCIP/INT, available from (ABCAM, Cambridge, Mass.)]. Direct labeling can be achieved by covalently conjugating a label molecule to the polynucleotide (e.g., using solid-phase synthesis) or by incorporation via polymerization (e.g., using an in vitro transcription reaction or random-primed labeling). Indirect labeling can be achieved by covalently conjugating or incorporating to the polynucleotide a non-labeled tag molecule (e.g., Digoxigenin or biotin) and subsequently subjecting the polynucleotide to a labeled molecule (e.g., anti-Digoxigenin antibody or streptavidin) capable of specifically recognizing the non-labeled tag.

The above-described polynucleotides can be employed in a variety of RNA detection methods such as Northern blot analysis, reverse-transcribed PCR (RT-PCR) [e.g., a semi-quantitative RT-PCR, quantitative RT-PCR using e.g., the Light Cycler™ (Roche)], RNA in situ hybridization (RNA-ISH), in situ RT-PCR stain [e.g., as described in Nuovo G J, et al. 1993, Intracellular localization of polymerase chain reaction (PCR)-amplified hepatitis C cDNA. Am J Surg Pathol.

17: 683-90, and Komminoth P, et al. 1994, Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract., 190: 1017-25] and oligonucleotide microarray analysis [e.g., using the Affymetrix microarray (Affymetrix®, Santa Clara, Calif.)].

As mentioned, a level of CD24 in a PBC sample above a predetermined threshold is indicative of the cancer or pre-malignant lesion.

The "predetermined threshold" may be experimentally determined by comparing normal PBC samples (e.g., samples obtained from healthy subjects) to PBC samples derived from subjects known to have carcinogenesis such as CRC. Preferably, a statistically significant number of samples are analyzed.

It will be appreciated that the presence of the cancer or the pre-malignant lesion can be further validated using additional assays. For example, in case the level of CD24 detected in a PBC sample of a subject is above a predetermined threshold, additional assays such as colon endoscopy followed by histological evaluations (including CD24 immunostaining) may be performed on the identified adenomas (in case adenomas are present).

The present inventors have also shown that subjects known to be at risk for cancer (e.g. have a family history), but do not actually have the cancer also show elevated levels of CDC24 in their blood—see FIG. 5.

Thus, according to another aspect of the present invention there is provided a method of determining a predisposition to cancer or a pre-malignant lesion, the method comprising determining a level of CD24 expressed on peripheral blood cells of a subject in need thereof, wherein the level of CD24 above a predetermined threshold is indicative of a predisposition to the cancer or the pre-malignant lesion.

It will be appreciated that the present teachings may also be used to determine treatment efficacy. Thus determining CD24 on PBC may be effected following and optionally prior to anti cancer treatment, whereby a reduction of CD24 on PBC is indicative of treatment efficacy.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Detection of CD24 in Human Samples

Study 1

In order to determine whether CD24 expressed in PBL cells might serve as a potential tumor biomarker in cancer, samples collected from 203 individuals, including healthy subjects, CRC patients, other tumors and disease states were screened. The "Other tumors" category includes lung, prostate, urinary tract and gynecological cancers.

Materials and Methods

Patient Population:

203 consecutive subjects attending the Integrated Cancer Prevention Center at Tel Aviv Medical Center were consented. Each subject filled a personal questionnaire, gave a blood sample and was subjected to a physical examination. All patients underwent colonoscopy. A detailed epidemiological questionnaire was filled by an expert member of the staff. The study included healthy (normal), adenomas and CRC subjects.

Blood Sample Preparation:

PBLs were isolated from whole blood samples by collecting white buffy coats obtained after blood centrifugation for 3 minutes at 3000 rpm and discarding the plasma supernatant.

Residual erythrocytes were lysed by brief incubation in erythrocyte lysis buffer (ELB) containing, 155 mM $NH_4Cl$, 0.1 mM EDTA, and 10 mM $KHCO_3$ followed by washing of the cells in the same buffer. The resulting pellet was lysed in the presence of 1% Triton X-100 and protease inhibitors (20 min on ice) and centrifuged at 15,000×g for 15 minutes, 4° C. The protein concentration in lysates was determined by BioRad assay and protein extracts (20 μg) were subjected to SDS-PAGE and Western blotting using the monoclonal anti-CD24 SWA11. Detection was performed by enhanced chemiluminescence (ECL) using a commercial kit (Biological Industries, Beit HaEmek, Israel).

Band intensities were quantitated by densitometry analysis using the imaging TINA 2.0 software.

Results

Representative results are presented in FIG. 1. All results (203 subjects) are summarized in Table 1.

TABLE 1

| Status | Description | CD24 Positive No. | Percentage | CD24 Negative No. | Percentage | Total |
|---|---|---|---|---|---|---|
| 0 | Normal | 54 | 47.4% | 60 | 52.6% | 114 |
| 1 | Adenoma/s | 12 | 63.2% | 7 | 36.8% | 19 |
| 2 | CRC | 33 | 71.7% | 13 | 28.3% | 46 |
| 3 | Pancreatic Can. | 2 | 66.7% | 1 | 33.3% | 3 |
| 4 | IBD | 2 | 50.0% | 2 | 50.0% | 4 |
| 5 | Barret's | 2 | 100.0% | 0 | 0.0% | 2 |
| 6 | Stomach Can. | 4 | 80.0% | 1 | 20.0% | 5 |
| 8 | Other tumors | 5 | 71.4% | 2 | 28.6% | 7 |
| 10 | Breast Cancer | 2 | 100.0% | 0 | 0.0% | 2 |
| 2, 8 | | 1 | 100.0% | 0 | 0.0% | 1 |
| Total | | 117 | | 86 | | 203 |

Table 2 summarizes the average age (Positive vs. Negative) of men and women screened.

TABLE 2

| | | Positive | | | | Negative | | | | |
|---|---|---|---|---|---|---|---|---|---|---|
| | | F | | M | | F | | M | | |
| Status | Description | No. | Av. Age | No. | Av. Age | No. | Av. Age | No. | Av. Age | Total |
| 0 | Normal | 26 | 56.4 | 28 | 55.5 | 36 | 49.7 | 24 | 53.0 | 114 |
| 1 | Adenoma/s | 3 | 74.3 | 9 | 61.1 | 1 | 58.0 | 6 | 56.0 | 19 |
| 2 | CRC | 13 | 67.1 | 20 | 58.3 | 6 | 57.5 | 7 | 73.3 | 46 |
| 3 | Pancreatic Cancer | 1 | 60.0 | 1 | 90.0 | | | 1 | 64.0 | 3 |
| 4 | IBD | | | 2 | 59.5 | | | 2 | 52.5 | 4 |
| 5 | Barret's | 2 | 68.0 | | | | | | | 2 |
| 6 | Stomach Cancer | 1 | 71.0 | 3 | 63.0 | 1 | 52.0 | | | 5 |
| 8 | Other tumors | 2 | 53.0 | 3 | 76.0 | 1 | 59.0 | 1 | 67.0 | 7 |
| 10 | Breast Cancer | 2 | 62.5 | | | 0 | | | | 2 |
| 2, 8 | | 1 | 55.0 | | | 0 | | | | 1 |
| Total | | 51 | | 66 | | 45 | | 41 | | 203 |

F—Females;
M—Males

As shown in Table 1, the percentage of CD24 positives in normal samples was relatively high (~50%). In addition, a low percentage of CRC cases tested (28.3%) appear to be CD24 negative. Therefore, in order to facilitate the detection of a diagnostic cut off value of CD24, a densitometry analysis of the bands shown in FIG. 1 was performed. Results are shown in FIG. 2.

Differences between CRC patients, adenomas and the normal group were statistically significant ($p<0.001$). High CD24 levels were also validated in preliminary studies in other tumors (pancreatic, gastric, breast, lung, prostate, urinary tract and gynecological cancers and Barret's esophagus) as compared to healthy controls.

Figure 3:
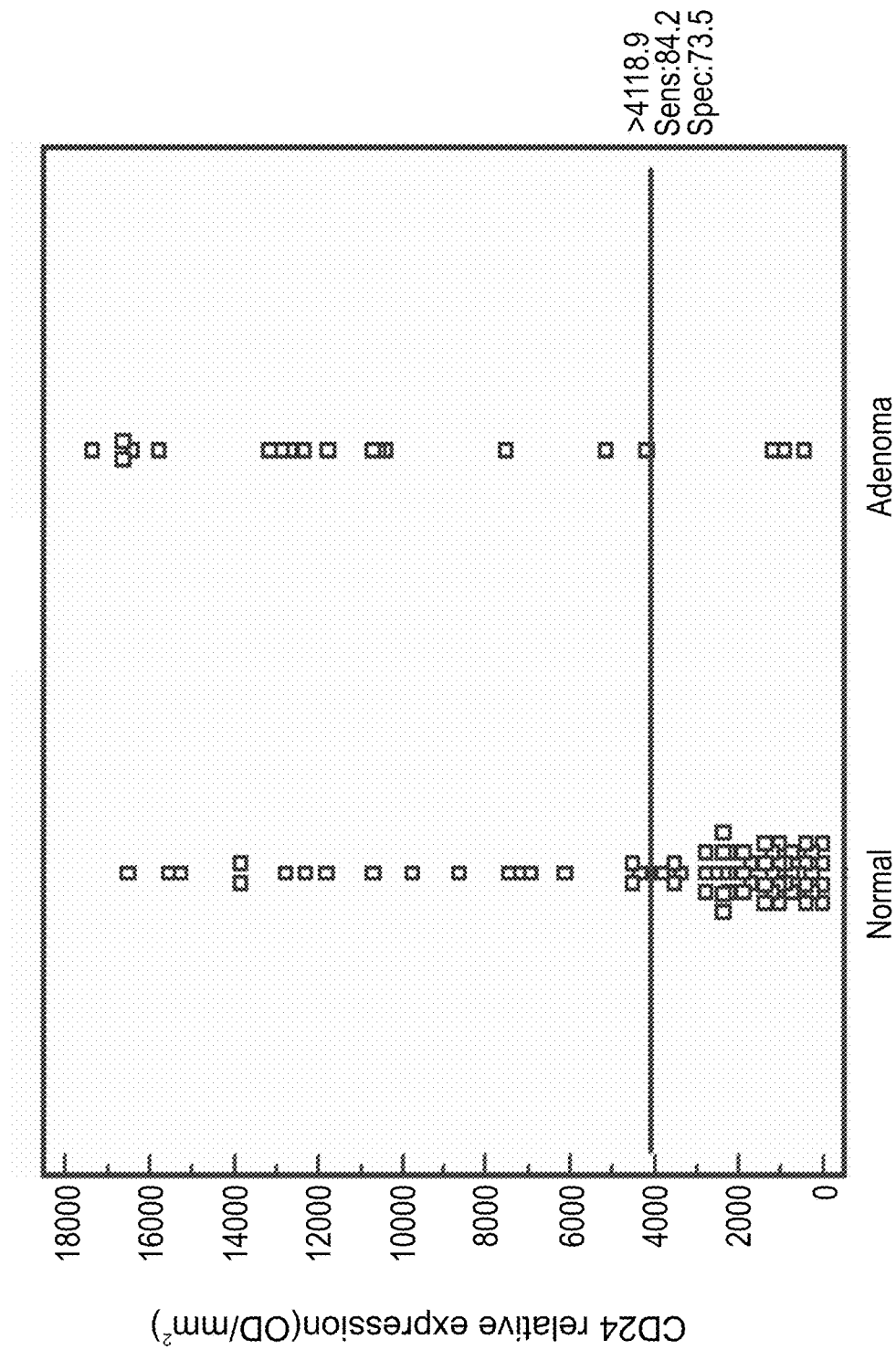
FIG. 3 is a graph of ROC analysis: Normal vs. Adenoma.
Figure 4:
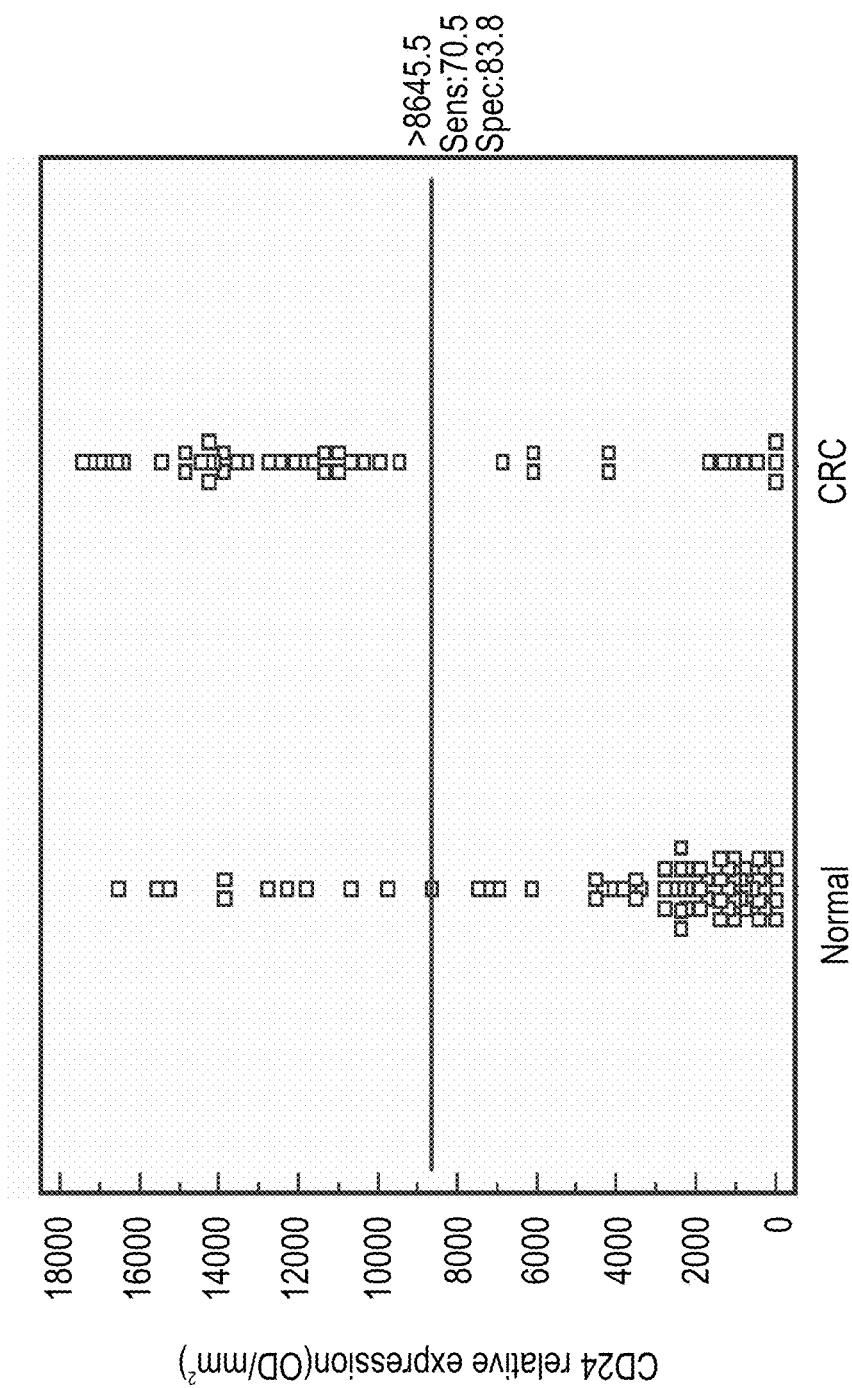
FIG. 4 is a graph of ROC analysis: Normal vs. CRC.

Receiver operating characteristic (ROC) analysis was used to determine the specificity and sensitivity of the CD24 test (Table 3, herein below), and its ability to discriminate patients with CRC (n=63) or adenoma (n=19) from normal individuals (n=68) with no clinical findings upon colonoscopy (FIGS. 3-4).

TABLE 3

| | Sensitivity | Specificity |
|---|---|---|
| Normal vs. Adenoma | 84.2 | 73.5 |
| Normal vs. CRC | 70.5 | 83.3 |

Example 2

Detection of CD24 in Human Samples

Study 2

In view of the above promising results a second (validation) study was conducted in which an additional 190 samples were tested.

Materials and Methods

Patient Population:

All patients underwent colonoscopy. Normal subjects with or without colonoscopy (status 0 or 00, respectively) were tested. Additional data was collected such as inflammation parameters (CRP levels and related clinical data), and family history of cancer. Thus, normal subjects with high CRP levels were not included, while normal subjects with a family history of cancer were included in a separated category.

Blood Sample Preparation:

Briefly, PBLs were isolated from whole blood samples by collecting white buffy coats obtained after blood centrifugation for 3 minutes at 3000 rpm and discarding the plasma supernatant. Residual erythrocytes were lysed by brief incubation in erythrocyte lysis buffer (ELB) containing, 155 mM $NH_4Cl$, 0.1 mM EDTA, and 10 mM $KHCO_3$ following by washing of the cells in the same buffer. The resulting pellet was lysed in the presence of 1% Triton X-100 and protease inhibitors (20 minutes on ice) and centrifuged at 15,000×g for 15 minutes, 4° C. The protein concentration in lysates was determined by BioRad assay and protein extracts (20 µg) were subjected to SDS-PAGE and Western blotting using anti-CD24 SWA11. Band intensities were quantitated by densitometry analysis using the imaging TINA 2.0 software as previously described. Densitometry results were plotted and subjected to statistical analysis for significance.

Results

Figure 6:
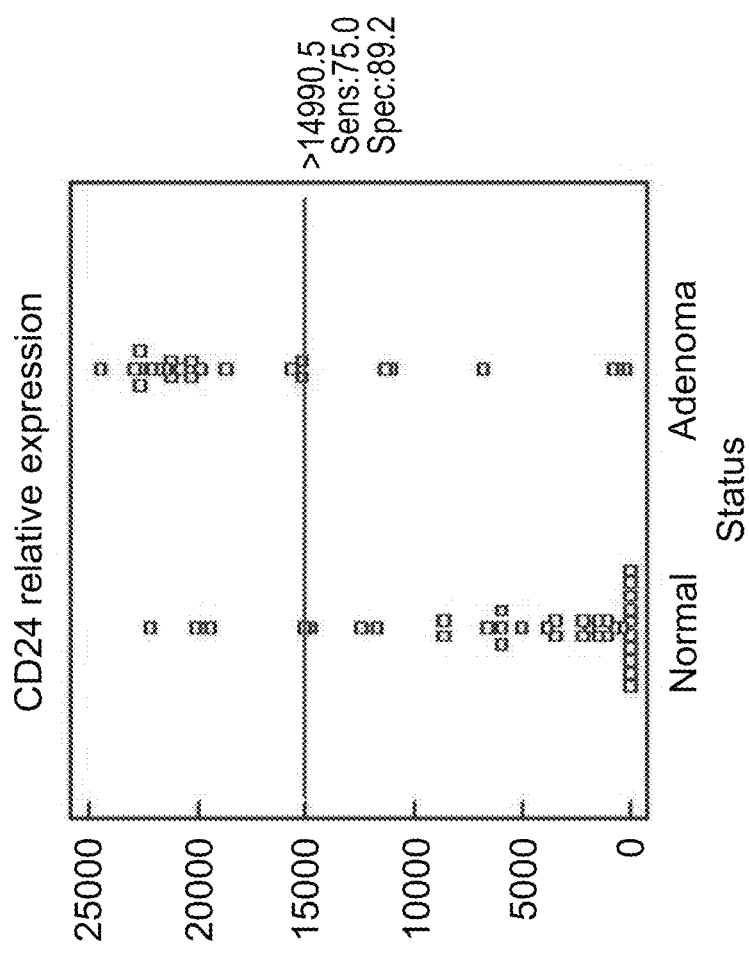
FIG. 6 is a graph of ROC analysis: Normal vs. Adenoma.
Figure 7:
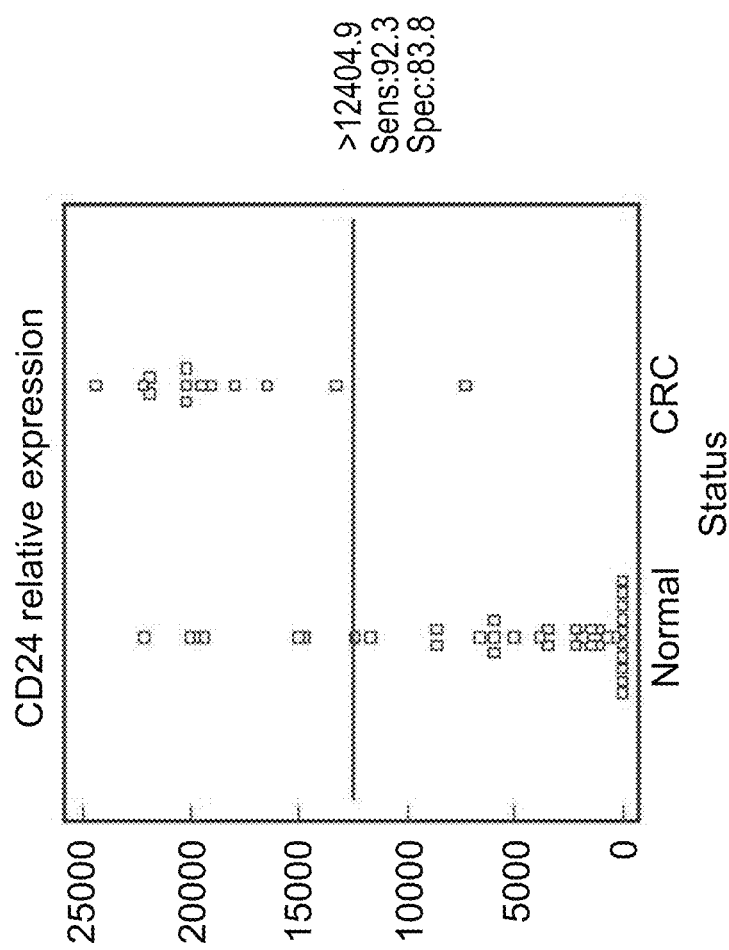
FIG. 7 is a graph of ROC analysis: Normal vs. CRC.

The results are presented in FIGS. 5-7 and Table 4, herein below.

TABLE 4

| | Sensitivity | Specificity |
|---|---|---|
| Normal vs. Adenoma | 75.0 | 89.2 |
| Normal vs. CRC | 92.3 | 83.8 |

In conclusion, the present data further support that CD24 is able to detect CRC with high reliability and may serve as a potential CD24 biomarker for CRC and for early stages of colorectal neoplasia.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Aigner, S., Sthoeger, Z. M., Fogel, M., Weber, E., Zarn, J., Ruppert, M., Zeller, Y., Vestweber, D., Stahel, R., Sammar, M., and Altevogt, P. CD24, a mucin-type glycoprotein, is a ligand for P-selectin on human tumor cells. Blood, 1997, 89: 3385-3395.
2. Aigner, S., Ramos, C. L., Hafezi-Moghadam, A., Lawrence, M. B., Friederichs, J., Altevogt, P., and Ley, K. CD24 mediates rolling of breast carcinoma cells on P-selectin. FASEB J. 1998, 12: 1241-1251.
3. Baumann P, Cremers N, Kroese F, Orend G, Chiquet-Ehrismann R, Uede T, Yagita H, Sleeman J P. CD24 expression causes the acquisition of multiple cellular properties associated with tumor growth and metastasis. Cancer Res. 2005; 65:10783-93.
4. Kanaoka S, Yoshida K, Miura N, Sugimura H, Kajimura M. Potential usefulness of detecting cyclooxygenase 2 messenger RNA in feces for colorectal cancer screening. Gastroenterology. 2004; 127(2): 422-7.
5. Kristiansen et al., 2004; J. of Mol. Hist. 35: 255-262.
6. Laken S J, Petersen G M, Gruber S B, Oddoux, Vogelstein B. Familial colorectal cancer in Ashkenazim due to a hypermutable tract in APC. Nat Genet. 17: 79-83, 1997.
7. Mandel J, Bond J, et al., 1993, Reducing mortality from colorectal cancer by screening for fecal occult blood. Minnesota Colon Cancer Control Study. N Engl J Med 1993: 328: 1365-71.
8. McMahon P M, Bosch J L, et al., 2001. Cost-effectiveness of colorectal cancer screening. Radiology, 219(1): 44-50.
9. Roessler M, Rollinger W, Palme S, Hagmann M L, et al., 2005. Identification of nicotinamide N-methyltransferase as a novel serum tumor marker for colorectal cancer. Clin Cancer Res. 2005 Sep. 15; 11(18):6550-7.
10. Roessler M., Rollinger W, Mantovani-Endl L., et al. Identification of PSME3 as a Novel Serum Tumor Marker for Colorectal Cancer by Combining Two-dimensional Polyacrylamide Gel Electrophoresis with a Strictly Mass Spectrometry-based Approach for Data Analysis. Molecular and Cellular Proteomics 5: 2092-2101, 2006.
11. Sagiv E., et al., 2006, Gastroenterology, 131: 630-639.
12. Sammar, M., Aigner, S., Hubbe, M., Schirrmacher, V., Schachner, M., Vestweber, D., and Altevogt, P. Heat-stable antigen (CD24) as ligand for mouse P-selectin. Int. Immunol. 1994, 6: 1027-1036.
13. Schabath H, Runz S, Joumaa S, Altevogt P. CD24 affects CXCR4 function in pre-B lymphocytes and breast carcinoma cells. J Cell Sci. 2006; 119:314-25.
14. Smith S C, Oxford G, Wu Z, Nitz M D, Conaway M, Frierson H F, Hampton G, Theodorescu D. The metastasis-associated gene CD24 is regulated by Ral GTPase and is a mediator of cell proliferation and survival in human cancer. Cancer Res. 2006; 66:1917-22.
15. Strul, H., Barenboim, M, Leshno, M. Gartner, R. Kariv, E. Aljadeff, Y. Aljadeff, D. Kazanov, L. Strier, A. Keidar, Y.

Knaani, Y. Degani, L. Alon-Baron, H. Sobol-Dvory, Z. Halpern, N. Arber. The I1307K adenomatous polyposis coli gene variant does not contribute in the assessment of the risk for colorectal cancer in Ashkenazi Jews. Cancer Epidemiol Biomarkers Prev 12:1012-1015, 2003.

16. Weichert W., et al. 2005; Clin. Cancer Res. 11: 6574-6581.
17. Zhou Q., et al. 2003, Proc. Natl. Acad. Sci. 100: 15041-15046.
18. U.S. Pat. Appl. 20040005596 to Li J., et al.

What is claimed is:

1. A method of diagnosing a gastrointestinal tract cancer or a pre-malignant lesion associated with a gastrointestinal tract cancer, the method comprising:
    (a) obtaining a blood sample of a subject in need thereof;
    (b) separating peripheral blood leukocytes (PBL) from said blood sample;
    (c) determining a level of anchored CD24 protein expressed on said PBL by detecting said anchored CD24 protein level in said PBL sample using a CD24 specific antibody, wherein said level of CD24 protein above a predetermined threshold is indicative of a diagnosis of the gastrointestinal tract cancer or the pre-malignant lesion associated with the gastrointestinal tract cancer; and
    (d) corroborating said diagnosis of gastrointestinal tract cancer or the pre-malignant lesion associated with the gastrointestinal tract cancer by colon endoscopy.

2. The method of claim 1, wherein said pre-malignant lesion is an adenoma.

3. The method of claim 1, wherein said determining is effected ex vivo.

4. The method of claim 1, wherein said gastrointestinal tract cancer is colorectal cancer.

5. The method of claim 1, wherein said gastrointestinal tract cancer is colorectal cancer.

6. The method of claim 1, wherein said separating is effected by centrifugation of blood samples and discarding of plasma.

7. The method of claim 1, wherein said separating is effected by buffy coats.

8. The method of claim 1, wherein said peripheral blood leukocytes (PBL) are non-activated PBL.

9. The method of claim 1, wherein said determining is by western blot or ELISA.

* * * * *

SEQUENCE LISTING

<160> NUMBER OF SEQ ID NOS: 2

<210> SEQ ID NO 1
<211> LENGTH: 80
<212> TYPE: PRT
<213> ORGANISM: Homo sapiens

<400> SEQUENCE: 1

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80
```

<210> SEQ ID NO 2
<211> LENGTH: 2194
<212> TYPE: DNA
<213> ORGANISM: Homo sapiens

<400> SEQUENCE: 2

```
gggtctcgcc ggctcgccgc gctccccacc ttgcctgcgc ccgcccggag ccagcggttc      60
tccaagcacc cagcatcctg ctagacgcgc cgcgcaccga cggaggggac atgggcagag     120
caatggtggc caggctcggg ctggggctgc tgctgctggc actgctccta cccacgcaga     180
tttattccag tgaaacaaca actggaactt caagtaactc ctcccagagt acttccaact     240
ctgggttggc cccaaatcca actaatgcca ccaccaaggc ggctggtggt gccctgcagt     300
caacagccag tctcttcgtg gtctcactct ctcttctgca tctctactct taagagactc     360
aggccaagaa acgtcttcta aatttcccca tcttctaaac ccaatccaaa tggcgtctgg     420
aagtccaatg tggcaaggaa aaacaggtct tcatcgaatc tactaattcc acaccttta     480 ttgacacaga aaatgttgag aatcccaaat ttgattgatt tgaagaacat gtgagaggtt     540
tgactagatg atggatgcca atattaaatc tgctggagtt tcatgtacaa gatgaaggag     600
aggcaacatc caaaatagtt aagacatgat ttccttgaat gtggcttgag aaatatggac     660
acttaatact accttgaaaa taagaataga aataaaggat gggattgtgg aatggagatt     720 cagtttttcat ttggttcatt aattctataa ggccataaaa caggtaatat aaaaagcttc     780
catgattcta tttatatgta catgagaagg aacttccagg tgttactgta attcctcaac     840
gtattgtttc gacagcacta atttaatgcc gatatactct agatgaagtt ttacattgtt     900
gagctattgc tgttctcttg ggaactgaac tcactttcct cctgaggctt tggatttgac     960
attgcatttg accttttatg tagtaattga catgtgccag ggcaatgatg aatgagaatc    1020
tacccccaga tccaagcatc ctgagcaact cttgattatc catattgagt caatggtag     1080 gcatttccta tcacctgttt ccattcaaca agagcactac attcatttag ctaaacggat    1140
tccaaagagt agaattgcat tgaccacgac taatttcaaa atgctttta ttattattat     1200
```

```
-continued ttttagaca gtctcacttt gtcgcccagg ccggagtgca gtggtgcgat ctcagatcag    1260
tgtaccattt gcctcccggg ctcaagcgat tctcctgcct cagcctccca agtagctggg    1320
attacaggca cctgccacca tgcccggcta attttgtaa ttttagtaga gacagggttt    1380
caccatgttg cccaggctgg tttcgaactc ctgacctcag gtgatccacc cgcctcggcc    1440
tcccaaagtg ctgggattac aggcttgagc ccccgcgccc agccatcaaa atgcttttta    1500
tttctgcata tgttgaatac tttttacaat ttaaaaaaat gatctgtttt gaaggcaaaa    1560
ttgcaaatct tgaaattaag aaggcaaaaa tgtaaaggag tcaaaactat aaatcaagta    1620
tttgggaagt gaagactgga agctaatttg cattaaattc acaaactttt atactctttc    1680
tgtatataca ttttttttct ttaaaaaaca actatggatc agaatagcca catttagaac    1740 acttttgtt atcagtcaat atttttagat agttagaacc tggtcctaag cctaaaagtg    1800
ggcttgattc tgcagtaaat cttttacaac tgcctcgaca cacataaacc tttttaaaaa    1860
tagacactcc ccgaagtctt ttgttcgcat ggtcacacac tgatgcttag atgttccagt    1920
aatctaatat ggccacagta gtcttgatga ccaaagtcct ttttttccat ctttagaaaa    1980
ctacatggga acaaacagat cgaacagttt tgaagctact gtgtgtgtga atgaacactc    2040
ttgctttatt ccagaatgct gtacatctat tttggattgt atattgtgtt tgtgtattta    2100
cgctttgatt catagtaact tcttatggaa ttgatttgca ttgaacacaa actgtaaata    2160
aaaagaaatg gctgaaagag caaaaaaaaa aaaa                               2194
```